United States Patent [19]
Wilkening

[11] Patent Number: 5,912,331
[45] Date of Patent: Jun. 15, 1999

[54] PROCESS FOR THE PREPARATION OF 9-DEOXO-9(Z)-HYDROXYIMINOERYTHROMYCIN A

[75] Inventor: Robert R. Wilkening, Maplewood, N.J.

[73] Assignee: Merck & Co., Inc., Rahway, N.J.

[21] Appl. No.: 07/669,809

[22] Filed: Mar. 15, 1991

[51] Int. Cl.$^6$ ................................... C07H 1/00
[52] U.S. Cl. ........................... 536/7.4; 536/18.5
[58] Field of Search .................... 536/7.4, 18.5

[56] References Cited

U.S. PATENT DOCUMENTS

| | | | |
|---|---|---|---|
| 3,869,444 | 3/1975 | Freiberg | 536/7.4 |
| 3,923,784 | 12/1975 | Kierstead et al. | 536/7.4 |
| 3,979,511 | 9/1976 | Hung et al. | 514/29 |
| 4,109,076 | 8/1978 | Henry et al. | 536/6.4 |
| 4,152,424 | 5/1979 | Kierstead et al. | 424/120 |
| 4,328,334 | 5/1982 | Kobrihel et al. | 536/7.4 |
| 4,349,545 | 9/1982 | Gouin d'Ambrieres et al. | 536/7.4 |
| 4,464,527 | 8/1984 | Bright | 536/7.4 |
| 4,465,674 | 8/1984 | Bright et al. | 514/29 |
| 4,492,688 | 1/1985 | Bright | 514/29 |
| 4,512,982 | 4/1985 | Hauske et al. | 514/29 |
| 4,517,359 | 5/1985 | Kobrehel et al. | 536/7.4 |
| 4,518,590 | 5/1985 | Hauske et al. | 514/29 |
| 4,526,889 | 7/1985 | Bright | 514/29 |
| 4,680,386 | 7/1987 | Morimoto et al. | 514/7.4 |
| 4,739,118 | 4/1988 | Elbe | 564/256 |
| 4,886,792 | 12/1989 | Djokic et al. | 514/183 |
| 4,921,839 | 5/1990 | Brain et al. | 514/29 |
| 4,957,905 | 9/1990 | Hunt | 514/29 |
| 4,990,602 | 2/1991 | Morimoto et al. | 536/7.4 |

FOREIGN PATENT DOCUMENTS

| | | |
|---|---|---|
| 0 101 186 | 2/1984 | European Pat. Off. . |
| 0 109 253 | 5/1984 | European Pat. Off. . |
| 0 136 831 | 10/1985 | European Pat. Off. . |
| 0 259 789 | 3/1988 | European Pat. Off. . |
| 0121701 | 8/1988 | European Pat. Off. . |
| 0 283 055 | 9/1988 | European Pat. Off. . |
| 0 298 650 | 1/1989 | European Pat. Off. . |
| 0 307 128 | 3/1989 | European Pat. Off. . |
| 0 316 128 | 5/1989 | European Pat. Off. . |

OTHER PUBLICATIONS

Journal of Antibiotics, vol. 40, No. 7, by S. Djokic, et al. (Jul. 1987).

J. Chem. Soc. Perkin Trans. 1, pp. 1881–1890, by S. Djokic, et al. (1986).

J. Chem. Research (S), pp. 152–153, by S. Djokic, et al. (1988).

The Journal of Antibiotics, vol. 61, No. 8, pp. 1029–1047, by Bright et al. (1988).

Tetrahedron Letters, No. 2, pp. 157–160 by E. H. Massey, et al., (1970).

The Journal of Antibiotics, vol. 44, No. 3, J.C. Gasc, et al. (1990) pp. 313–329.

J. Org. Chem., 39, (1974) Egan, et al., pp. 2492–2494.

Antimicrobic Newsletter, vol. 4, No. 4 (1987) Thornsberry, et al., pp. 25–36.

*Primary Examiner*—Elli Peselev
*Attorney, Agent, or Firm*—Sylvia A. Ayler; Mark R. Daniel

[57] ABSTRACT

A method is presented for isomerizing the E-isomer of 9-Deoxo-9-hydroximinoerythromycin A to its corresponding Z-isomer. The Z-isomer is useful as an antibiotic and as an intermediate for the synthesis of other macrolide antibiotics.

1 Claim, No Drawings

PROCESS FOR THE PREPARATION OF 9-DEOXO-9(Z)-HYDROXYIMINOERYTHROMYCIN A

BACKGROUND OF THE INVENTION

The present invention relates to a novel method of preparing a novel chemical compound having antibacterial activity, which is useful in the therapy of bacterial infections in mammals. The compound is also itself useful as an intermediate in the synthesis of other antibacterial compounds. More specifically, the method of preparation of the present invention relates to derivatives of the well-known macrolide antibiotic, erythromycin A, the compound of the structure:

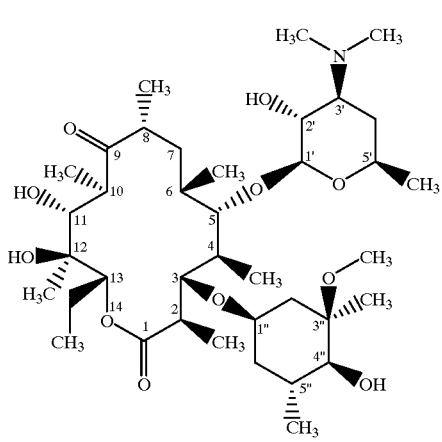

(I)

Even more specifically, the invention relates to a method of making 9-deoxo-9(Z)-hydroxy-iminoerythromycin A, the compound of the structure:

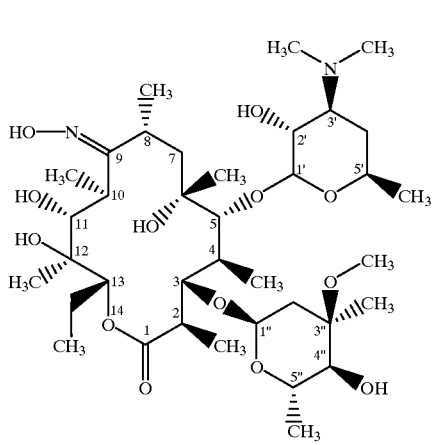

(II)

The (Z) geometric isomer of erythromyein A oxime has been unobtainable until now, with only the (E) geometric isomer having been previously achieved.

The C-9 carbonyl group of erythromycin A has been the focus of considerable chemical modification. For example, the ketone has been reduced to the 9-hydroxy derivative, and has been condensed with hydroxylamine and hydrazine to provide the corresponding oxime and hydrazone derivatives M. V. Sigal, Jr., P. F. Wiley, K. Gerzon, E. H. Flynn, U. C. Quark, and O. Weaver, J. Am. Chem. Soc., 1956, 78, 388. E. H. Massey, B. Kitchell, L. D. Martin, K. Gerzon, and H. W. Murphy, Tetrahedron Lett., 1970, 157. Of all the modifications at C-9, the oxime derivative is perhaps the most valuable substance both in terms of its antibacterial properties and as a substrate for further chemical modification. Alkylation of the oxime group has provided a variety of biologically interesting 9-alkoxyimino derivatives which includes the clinical candidate roxithromycin U.S. Pat. No. 4,349,545. The oxime group has also been reduced to the corresponding 9-imino and 9-amino derivatives, (4) G. H. Timms and E. Wildsmith, Tetrahedron Lett., 1971, 195 which have in turn served as platforms for further synthetic manipulation. A particularly promising derivative of the 9(S)-amino isomer is the clinical candidate dirithromycin. More recently, Beckmann rearrangement of erythromycin A oxime has led to a series of ring expanded 9a-aza-9a-homoerythromycin analogs possessing interesting antibacterial properties and improved pharmacokinetic properties S. Djokic, G. Kobrehel, G. Lazarevski, N. Lopotar, and Z. Tamburasev, J. Chem. Soc. Perkin Trans. I, 1986, 1881. A particularly valuable member of this series is the clinical candidate azithromycin.

The configuration of the oximino group in erythromycin A oxime has been assigned as (9E) based on comparison of its proton nuclear magnetic resonance ($^1$H NMR) spectrum with that of the major isomer of erythromycin B oxime R. S. Egan, L. A. Freiberg, and W. H. Washburn, J. Org. Chem., 1974, 39, 2492. The erythromycin B series differs from the erythromycin A series in that the 12-hydroxy group has been replaced by a hydrogen atom. In the erythromycin B series, a minor, unstable (9Z) oxime isomer was isolated and characterized by $^1$H NMR, $^{13}$C NMR and infrared spectroscopy. To date, this remains the first and only report of the isolation and characterization of an erythromycin Z-oxime ibid. Similar attempts to determine the configuration of the Z-form of erythromycin A oxime were thwarted by the unavailability of an isolable, minor isomer.

The present invention relates to a process for isomerizing the (9E)-isomer of erythromycin A oxime to the corresponding (9Z)-isomer and for isolating the heretofore unknown (9Z)-isomer as a stable, crystalline substance. Like the (9E)-isomer discussed above, the (9Z)-isomer also possesses antibacterial activity and serves as a substrate for further chemical modification leading to new products.

SUMMARY OF THE INVENTION

In a single step procedure, 9-deoxo-9(Z)-hydroxyimininoerythromycin A of the structure:

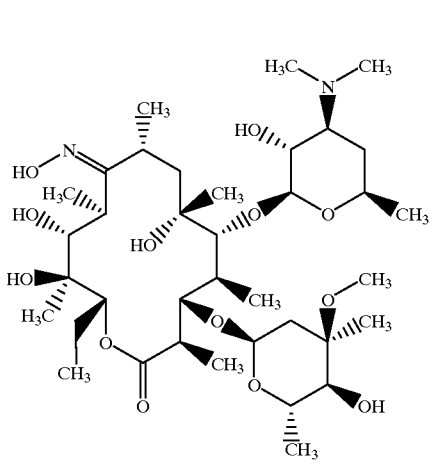

(II)

is obtained by reacting 9-deoxo-9(E)-hydroxyimino-erythromycin A of the structure:

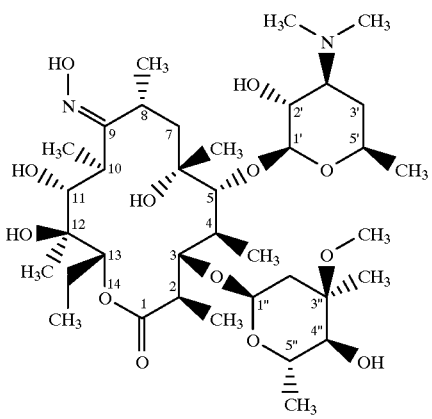

(III)

with a base in the presence of a protic or an aprotic solvent. Preferably, the base is an alkali metal hydroxide and the solvent is an alcohol. Most preferably, the base is lithium hydroxide (as the monohydrate) and the solvent is ethanol.

DETAILED DESCRIPTION OF THE INVENTION

Optimization of the method of the present invention requires a base and solvent combination of solvent sufficient basicity to substantially deprotonate the hydroxyimino group at position 9 of (III). Furthermore, the oxime anion must be reasonably stable under the reaction conditions for the time period required to complete the isomerization process, again by employing an appropriate base and solvent combination. Upon addition of the base to (III), an equilibrium condition is created as shown in the following equation:

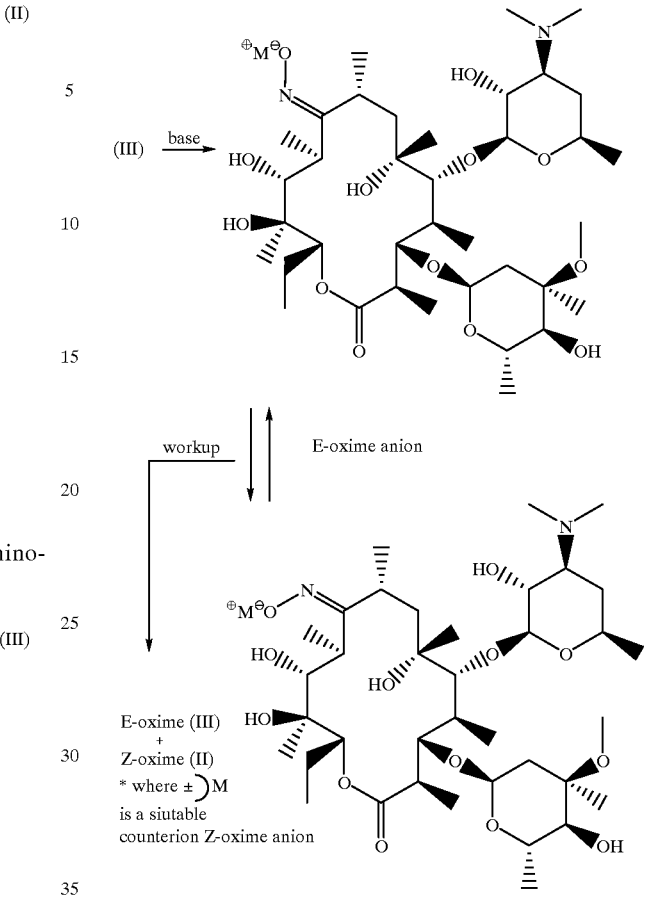

The workup performed on the anions includes protonation of the oxime anions to give the neutral oxime product mixture from which the desired Z-isomer is isolated by crystallization or by chromatography followed by crystallization.

The relative amounts of E and Z oxime anions (and neutral oximes after the workup) in the equilibrium mixture can be controlled and depends on a number of factors. These include (a) the strength and quantity of the base reagent, (b) the size of the counterion M, (c) the reaction solvent, and (d) the reaction temperature.

Suitable bases include hydroxides, alkoxides, carbonates, metal amides, amines and metal hydrides.

The following list of reagents is given to illustrate suitable bases and solvents, although the list is not to be taken as exhaustive and other bases and solvents known to those of ordinary skill in the art are not excluded. Preferred bases and solvents are indicated by an asterisk and most preferred bases are indicated by a dagger.

Bases

1. Hydroxides

| | | | |
|---|---|---|---|
| * | † | LiOH | lithium hydroxide |
| * | † | NaOH | sodium hydroxide |
| * | | KOH | potassium hydroxide |
| | | CsOH | cesium hydroxide |
| | | Ca(OH)$_2$ | calcium hydroxide |
| | | Mg(OH)$_2$ | magnesium hydroxide |

-continued

| | | | |
|---|---|---|---|
| | * | Me₄NOH | tetramethylammonium hydroxide |
| | | BnMe₃NOH | benzyltrimethylammonium hydroxide |
| | * | Et₄NOH | tetraethylammonium hydroxide |
| | | Bu₄NOH | tetrabutylammonium hydroxide |
| 2. | Alkoxides | | |
| | * † | LiOMe | lithium methoxide |
| | * † | LiOEt | lithium ethoxide |
| | | LiOiPr | lithium isopropoxide |
| | | LiOnBu | lithium n-butoxide |
| | | LiOsBu | lithium sec-butoxide |
| | * † | NaOMe | sodium methoxide |
| | * † | NaOEt | sodium ethoxide |
| | | NaOPr | sodium n-propoxide |
| | | NaOiPr | sodium iso-propoxide |
| | | NaOnBu | sodium n-butoxide |
| | | NaOsBu | sodium sec-butoxide |
| | | NaOtBu | sodium tert-butoxide |
| | | NaOSiMe₃ | sodium trimethylsilanolate |
| | | KOMe | potassium methoxide |
| | * | KOEt | potassium ethoxide |
| | | KOtBu | potassium tert-butoxide |
| | | KOSiMe₃ | potassium trimethylsilanoate |
| | | KOsBu | potassium sec-butoxide |
| | | CsOtBu | cesium tert-butoxide |
| | | Ca(OMe)₂ | calcium methoxide |
| | * | Mg(OEt)₂ | magnesium ethoxide |
| | | Ti(OEt)₄ | titanium (IV) ethoxide |
| | | Ti(OiPr)₄ | titanium (IV) isopropoxide |
| | | BnMe₃NOMe | benzyltrimethylammonium-methoxide |
| 3. | Carbonates | | |
| | | K₂CO₃ | potassium carbonate |
| | * | Cs₂CO₃ | cesium carbonate |
| | | Na₂CO₃ | sodium carbonate |
| 4. | Amides (for use in aprotic solvents) | | |
| | | LiNH₂ | lithium amide |
| | | LiNMe₂ | lithium dimethylamide |
| | * | LiNiPr₂ | lithium diisopropylamide |
| | | LiN(C₆H₁₁)₂ | lithium dicyclohexylamide |
| | | LiN(SiMe₃)₂ | lithium bis(trimethylsilyl) amide |
| | | NaNH₂ | sodium amide |
| | | KN(SiMe₃)₂ | potassium bis(trimethylsilyl) amide |
| 5. | Amines | | |
| | * | TMG | 1,1,3,3-tetramethyl guanidine |
| | | DBU | 1,8-diazabicyclo [5.4.0] undec-7-ene |
| | | proton sponge | 1,8-bis(dimethylamino)-naphthalene |
| 6. | Hydrides (for use in aprotic solvents) | | |
| | | LiH | lithium hydride |
| | * | NaH | sodium hydride |
| | | KH | potassium hydride |
| 7. | Solvents | | |
| | a. | Protic | |
| | | H₂O (generally used in combination with an alcohol solvent) | |
| | * † | MeOH | methanol |
| | * † | EtOH | ethanol |
| | * | iPrOH | isopropanol |
| | | n-BuOH | normal-butanol |
| | | s-BuOH | sec-butanol |
| | | t-BuOH | tert-butanol |
| | b. | Aprotic | |
| | | i. Nonpolar (as a group, these are generally used in combination with a protic or polar solvent) | |
| | | Et₂O | diethyl ether |
| | | THF | tetrahydrofuran |
| | | DME | dimethoxyethane |
| | | PhMe | toluene |
| | | CH₂Cl₂ | dichloromethane |
| | | CHCl₃ | chloroform |
| | | ii. Polar | |
| | * | DMF | dimethylformamide |
| | | DMAC | dimethylacetamide |
| | | DMI | 1,3-dimethyl-2-imidazolidinone |
| | * | NEP | 1-ethyl-2-pyrrolidinone |
| | | NMP | 1-methyl-2-pyrrolidinone |
| | | HMPA | hexamethylphosphoramide |
| | | MeNO₂ | nitromethane |
| | * | MeCN | acetonitrile |
| | | dioxane | |
| | | pyridine | |
| | * | DMSO | dimethyl sulfoxide |

Preferably, the reaction of the present invention is carried out at a concentration of 1–25% w/v of E-oxime to solvent, and most preferably at 10% w/v. The amount of base used is preferably 1.0–10.0 molar equivalents based on the amount of starting E-oxime more preferably 1.0–3.0 molar equivalents, and most preferably 2.0 molar equivalents. The reaction is generally run at a temperature of from 0° C. to 80° C., and more preferably at 22–25° C. The reaction can be allowed to run for 0.5 hours—20 days, but most preferably is carried out over 20–24 hours.

The following examples further illustrate details for the practice of the invention. Those skilled in the art will readily understand that known variations, when taken with the alternative bases and solvents taught above, can be used in the practice of the invention.

EXAMPLE 1

Preparation of 9-Deoxo-9(E)-hydroxyiminoerythromycin A

Hydroxylamine hydrochloride (224 g, 3.23 mol) was added to a solution of erythromycin A (100 g, ca. 95% pure, 0.129 mol, available from Aldrich Chemical Co. Inc., Milwaukee, Wis.) in pyridine (500 mL). The resulting mixture was stirred at room temperature for 27 hours, and then concentrated under vacuum at ca. 40° C. The semi-solid residue was kept under high vacuum overnight, then stirred with ethanol (600 mL) for 15 minutes and filtered. The collected solids were washed with hot (50° C.) ethanol. The combined filtrate and washing was evaporated under vacuum to a pale blue foam. The foam was shaken with water (850 mL) to give a thick emulsion which was stirred rapidly at room temperature for 2.5 hours to give a filterable precipitate. The precipitate was collected, washed with water (150 mL), and dried under vacuum to give a white solid (117.7 g).

The crude oxime hydrochloride was suspended in 5% aqueous sodium bicarbonate (1000 mL) and methylene chloride (1000 mL), and the mixture was stirred while the pH was adjusted to 9.5 by addition of 5N aqueous sodium hydroxide. The layers were separated and the aqueous portion was extracted with ethyl acetate (500 mL) and ethyl ether (500 mL). The combined organic layer and extracts were dried over sodium sulfate, filtered, and evaporated under vacuum to a white solid (92.3 g). The solid was dissolved in hot ethyl acetate (250 mL), and the solution diluted with hot hexanes (400 mL) and left overnight in a refrigerator. The crystals of 9-deoxo-9(E)-hydroxyiminoerythromycin A were collected, washed with ice-cold hexane (250 mL), and dried under vacuum to afford a white solid (88.5 g).

IR (CH₂Cl₂) 3560, 3400 (br), 2980, 2950, 1735, 1460, 1389, 1165, 1110, 1085, 1050, and 1010 cm⁻¹.

¹H NMR (CDCl₃) δ 5.05 (dd, H-13), 4.90 (d, H-1"), 4.38 (d, H-1'), 4.01 (m, H-5"), 3.99 (d, H-3), 3.74 (m, H-8), 3.66 (s, H-11), 3.54 (d, H-5), 3.45 (m, H-5'), 3.28 (s, OCH₃), 3.23 (dd, H-2'), 2.96 (t, H-4"), 2.87 (m, H-2), 2.64 (q, H-10), 2.43 (m, H-3'), 2.32 (d, H-2"eq), 2.27 (s, N(CH₃)₂), 1.98 (m, H-4), 1.87 (m, H-14a), 1.63 (m, H-4'eq), and 1.46 (s, 6-CH₃).

1H NMR (CD₃OD) δ 5.19 (dd, H-13), 4.48 (d, H-1'), 4.15 (dq, H-5"), 3.98 (d, H-3), 3.76 (m, H-8), 3.70 (m, H-5'), 3.67 (s, H-11), 3.58 (d, H-5), 3.33 (s, OCH₃), 3.23 (dd, H-2'), 3.01 (d, H-4"), 2.92 (m, H-2), 2.72 (m, H-10), 2.70 (m, H-3'), 2.43 (d, H-2"eq), 2.33 (s, N(CH₃)₂), 2.01 (m, H-4), 1.88 (m, H-14a), 1.72 (m, H-4'eq), 1.58 (dd, H-2"ax), 1.48 (m, H-14b), 1.45 (s, 6-CH₃), 1.26 (d, 5"-CH₃), 1.23 (s, 3"-CH₃), 1.14 (s, 12-CH₃), 1.10 (d, 4-CH₃), 1.05 (d, 8-CH₃), and 0.84 (t, CH₂CH₃).

¹³C NMR (CDCl₃) δ 175.3, 171.3, 103.1, 96.3, 83.5, 80.3, 78.1, 77.1, 75.1, 74.3, 72.6, 71.2, 70.9, 68.8, 65.4, 65.3, 49.4, 44.6, 40.3, 38.8, 37.8, 35.1, 32.6, 29.2, 27.0, 25.4, 21.5, 21.3, 18.7, 18.6, 16.3, 14.3, 10.6, and 9.3.

¹³C NMR (CD₃OD) δ 177.5, 171.6, 104.0, 98.0, 84.2, 81.2, 79.3, 78.3, 76.3, 74.2, 72.9, 72.2, 69.0, 66.7, 65.2, 50.0, 46.3, 40.7, 39.3, 36.2, 32.0, 27.4, 26.7, 22.3, 22.0, 21.6, 19.3, 19.1, 17.3, 16.6, 14.8, 11.2, and 10.2.

EI Mass Spectrum, m/e 748, 590, 574, 462, 431, 416, 398, 174, 159, 158, and 116.

EXAMPLE 2

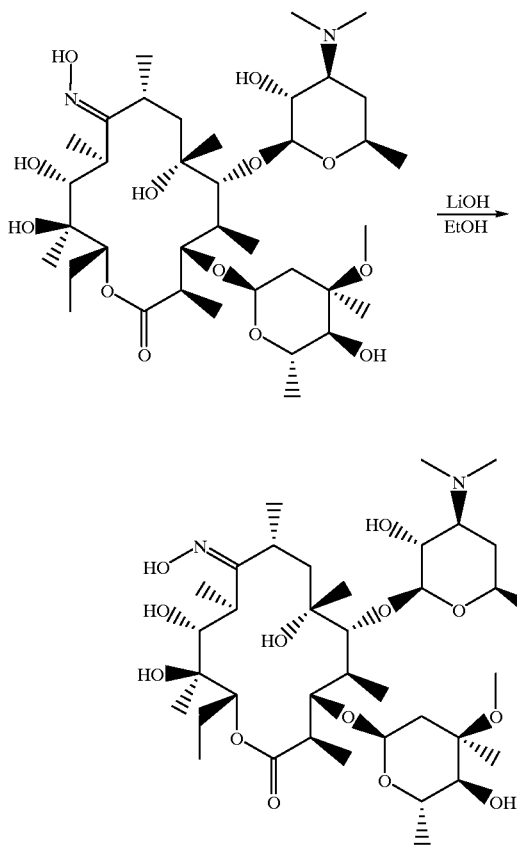

Conversion of 9-Deoxo-9(E)-hydroxyiminoerythromycin A to 9-Deoxo-9(Z)-hydroxyiminoerythromycin A Method 1:

9-Deoxo-9(E)-hydroxyiminoerythromycin A (20.0 g, 26.7 mMol) was added to a stirred solution of lithium hydroxide monohydrate (2.25 g, 53.5 mMol) in absolute ethanol (200 mL). The solution was blanketed with nitrogen and stirred overnight at room temperature. The solvents were evaporated under vacuum and the residue was partitioned between ethyl acetate (200 mL) and brine (120 mL). The pH of the mixture was adjusted from 11 to 9.3 with 2N hydrochloric acid. The ethyl acetate was removed and the brine was re-extracted with more ethyl acetate (2×200 mL). The combined ethyl acetate extracts were washed with brine (100 mL), dried with anhydrous magnesium sulfate, filtered and evaporated under vacuum to a foam (ca. 20 g).

The crude oxime mixture was dissolved in methylene chloride (220 mL) and stirred for 1 hour at room temperature to give a filterable, white solid (18.7 g). This material was dissolved in ethyl acetate (100 mL), diluted with nitromethane (100 mL), and 50 mL of solvent was evaporated under vacuum. Additional nitromethane (50 mL) was added and 80 mL of solvent was evaporated under vacuum. The solution was seeded with the 9(Z)-isomer and stirred at room temperature for 3 hours. The resulting suspension was filtered and the solids were rinsed with nitromethane (20 mL) and dried under a stream of nitrogen to afford 9-deoxo-9(Z)-hydroxyiminoerythromycin A (14.8 g, 74% yield) as a white solid.

MP 157–164° C.; IR (CHCl₃) 3680, 3435 (br), 2970, 2940, 1725, 1455, 1375, 1345, 1165, 1105, 1085, 1045, 1005, and 950 cm⁻¹.

1H NMR (CDCl₃) δ 5.01 (dd, H-13), 4.87 (d, H-1"), 4.40 (d, H-1'), 3.98 (m, H-3 and H-5"), 3.80 (s, H-11), 3.49 (m, H-5 and H-5'), 3.27 (s, OCH₃), 3.21 (dd, H-2'), 2.99 (m, H-4"), 2.8 (m, H-8, H-2 and H-10), 2.74 (m, H-10), 2.43 (m, H-3'), 2.32 (d, H-2"eq), 2.27 (s, N(CH₃)₂), 1.91 (m, H-4), 1.87 (m, H-14a), 1.63 (n, H-4'eq), 1.51 (m, H-2"ax and H-7), 1.42 (m, H-14b), 1.37 (s, 6-CH₃), 1.28 (d, 10-CH₃), 1.24 (d, 5"-CH₃), 1.19 (s, 3"-CH₃), 1.18 (d, 5'-CH₃), 1.12 (d, 2-CH₃), 1.11 (s, 12-CH₃), 1.08 (d, 8-CH₃), 1.04 (d, 4-CH₃), and 0.79 (t, CH₂CH₃).

¹H NMR (CD₃OD) δ 5.20 (br d, H-13), 4.50 (br d, H-1'), 4.16 (dq, H-5"), 4.02 (d, H-3), 3.70 (m, H-5'), 3.56 (br d, H-5), 3.34 (s, OCH₃), 3.25 (dd, H-2'), 3.03 (d, H-4"), 2.87 (m, H-8), 2.84 (m, H-2), 2.73 (m, H-3'), 2.44 (d, H-2"eq), 2.33 (s, N(CH₃)₂), 1.97 (m, H-4), 1.88 (m, H-14a), 1.73 (m, H-4'eq), 1.64 (m, H-7), 1.59 (dd, H-2"ax), 1.47 (m, H-14b), 1.36 (br s, 6-CH₃), 1.28 (d, 5"-CH₃), 1.24 (s, 3"-CH₃), 1.18 (m, 5'-CH₃, 2-CH₃, 8-CH₃ and 10-CH₃)), 1.13 (s, 12-CH₃), 1.08 (d, 4-CH₃), and 0.86 (t, CH₂CH₃).

¹³C NMR (CDCl₃) δ 176.2, 168.2, 102.8, 95.9, 83.6 (br), 79.3 (br), 77.9, 77.3, 75.2, 75.1, 72.7, 71.0, 70.9, 68.8, 65.5, 65.3, 49.4, 40.2, 39.9 (br), 37.8 (br), 35.7 (br), 34.9, 34.1 (br), 28.9, 26.0 (br), 21.4, 21.3, 19.8 (br), 18.4, 16.8, 15.3 (br), 10.7, and 9.2.

¹³C NMR (CD₃OD) δ 177.7, 170.0, 103.9, 97.7, 84.3 (br), 80.7, 79.2, 78.1, 77.0 (br), 76.1, 74.1, 72.8, 71.7 (br), 69.2, 66.7, 65.1, 49.9, 46.2 (br), 41.8 (br), 40.8, 40.5 (br), 36.0, 33.8 (br), 31.9, 26.7 (br), 22.8, 21.8, 21.7 (br), 21.6, 19.1, 17.5, 15.8 (br), 12.2 (br), 11.3, and 10.1.

FAB mass spectrum, m/e 749, 591, 416, 398, 174, 159, 158, and 116.

Elemental Analysis; Calculated for C₃₇H₆₈N₂O₁₃: C, 59.34; H, 9.15; N, 3.74. Found: C, 59.12; H, 8.80; N, 3.82.

Method 2: 1.0 LiOH in EtOH

9-Deoxo-9(E)-hydroxyiminoerythromycin A (255 mg, 0.34 mmol) was added to a solution of lithium hydroxide monohydrate (14.3 mg, 0.34 mmol) in absolute ethanol (2.55 mL). The resulting solution was stirred at room temperature for 25 hours, and then stored in a freezer at −20° C. for 68 hours. After warming to room temperature, the solution was evaporated under reduced pressure to remove the solvent. The residue was stirred with saturated aqueous sodium chloride (5 mL) and ethyl acetate (5 mL) while the pH was adjusted to 9.2 by addition of dilute hydrochloric acid. After shaking, the phases were separated and the aqueous portion extracted with more ethyl acetate (2×2.5 mL). The combined ethyl acetate extracts were washed with saturated sodium chloride solution (4 mL), dried over magnesium sulfate, filtered and evaporated at reduced pressure to afford a white foam (263 mg). Examination of this material by $^1$H NMR spectroscopy revealed a 31:69 mixture of 9-deoxo-9(E)-hydroxyiminoerythromycin A and 9-deoxo-9(Z)-hydroxyiminoerythromycin A.

Method 3: 2.0 LiOH in EtOH

9-Deoxo-9(E)-hydroxyiminoerythromycin A (291 mg, 0.333 mmol) was added to a solution of lithium hydroxide (32.6 mg, 0.776 mmol) in absolute ethanol (2.9 mL). The resulting solution was stirred at room temperature and under a nitrogen atmosphere for 22.5 hours. The solvent was evaporated at reduced pressure and the residue stirred with ethyl acetate (5 mL) and saturated aqueous sodium chloride (5 mL) while adjusting the pH to 9 by addition of 2N hydrochloric acid. The mixture was shaken, the phases separated, and the aqueous portion extracted with more ethyl acetate (2×2.5 mL). The combined ethyl acetate extracts were washed with saturated sodium chloride solution (4 mL), dried with magnesium sulfate, filtered and evaporated under vacuum to a white foam (299 mg). This material was shown by $^1$H NMR to be a 21:79 mixture of 9-deoxo-9(E)-hydroxyiminoerythromycin A and 9-deoxo-9(Z)-hydroxyiminoerythromycin A.

Method 4: 3.0 LiOH in EtOH

9-Deoxo-9(E)-hydroxyiminoerythromycin A (239 mg, 0.319 mmol) was was added to a mixture of lithium hydroxide monohydrate (40.2 mg, 0.957 mmol) in absolute ethanol (2.4 mL), and the resulting solution was stirred at room temperature and under a nitrogen atmosphere for 21.7 hours. Workup as described in method 3 afforded a white foam (236 mg) shown by $^1$H NMR to consist of a 19:81 mixture of 9-deoxo-9(E)-hydroxyiminoerythromycin A and 9-deoxo-9(Z)-hydroxyiminoerythromycin A.

Method 5: 2.0 NaOEt in EtOH

Freshly cut sodium metal (48 mg, 2.087 mmol) was dissolved in absoute ethanol (7.8 mL) under a nitrogen atmosphere. 9-Deoxo-9(E)-hydroxyiminoerythromycin A (782 mg, 1.043 mmol) was added and the resulting solution was stirred at room temperature. A crystalline precipitate, identified as the starting oxime by thin layer chromatography, appeared after a few hours. After stirring overnight, the mixture was once again a clear solution. After 54 hours, approximately half (3.9 mL) of the reaction mixture was removed and evaporated under reduced pressure. The gummy residue was stirred with ethyl acetate (5 mL) and saturated aqueous sodium chloride (5 mL) while the pH was adjusted to 9.2 by addition of dilute hydrochloric acid (2N and 0.2N solutions). The mixture was shaken, the layers separated, and the aqueous portion extracted with more ethyl acetate (2×2.5 mL). The combined ethyl acetate solution was washed with saturated brine (5 mL), dried with magnesium sulfate, filtered and evaporated under reduced pressure to a white foam (361 mg). This material was shown by $^1$H NMR spectroscopy to consist of a 22:78 mixture of the 9(E) and 9(Z) isomers of 9-deoxo-9-hydroxyiminoerythromycin A.

Method 6: 2.0 NaOH in EtOH

The remaining half of the reaction mixture from method 5 was treated with water (0.0188 mL, 1.04 mmol) to give a solution effectively consisting of sodium hydroxide and oxime in ethanol. The solution was stirred at room temperature for 23 hours, then worked up as described in method 5 to give a white foam (402 mg). This material was shown by $^1$H NMR to consist of a 24:76 mixture of the 9(E) and 9(Z) isomers of 9-deoxy-9-hydroxyiminoerythromycin A.

Method 7: 2.0 LiOH in MeOH

A solution of lithium hydroxide monohydrate (37 mg, 0.88 mmol), 9-deoxo-9(E)-hydroxyiminoerythromycin A (330 mg, 0.44 mmol), and methanol (3.3 mL) was stirred at room temperature for 65.5 hours. The solution was then stored at −20° C. for 13 days before warming to room temperature and evaporating the solvent at reduced pressure. The residue was stirred with ethyl acetate (5 mL) and saturated brine (5 mL) while adjusting the pH to 9.2 by addition of dilute hydrochloric acid. The mixture was shaken, the layers separated and the aqueous portion extracted with more ethyl acetate (2×2.5 mL). The combined ethyl acetate solution was washed with saturated brine (5 mL), dried with magnesium sulfate, and evaporated under vacuuum to provide a white foam (324 mg). NMR analysis of this material indicated a 45:55 ratio of 9(E) to 9(Z) 9-deoxo-9-hydroxyiminoerythromycin A products.

Method 8: 2.0 NaOMe in MeOH

A solution of 9-deoxo-9(E)-hydroxyiminoerythromycin A (375 mg, 0.5 mmol) in anhydrous methanol (3.5 mL) was cooled in an ice bath and stirred under a nitrogen atmosphere while methanolic sodium methoxide (0.23 mL of a 25 wt % solution, 1.01 mmol) was added by syringe. The cooling bath was removed and the solution was stirred at room temperature and under a nitrogen atmosphere for 66 hours. The solution was then stored at −20° C. for 13.3 days before being processed to a white foam (329 mg) as described in method 7. The product consisted of a 35:65 mixture of 9-deoxo-9(E)-hydroxyiminoerythromycin A and 9-deoxo-9 (Z)-hydroxyiminoerythromycin A as determined by $^1$H NMR spectroscopy.

Method 9: 10.0 NaOMe in MeOH

A solution of 9-deoxo-9(E)-hydroxyiminoerythromycin A (100 mg, 0.134 mmol) in anhydrous methanol (4.70 mL) was treated with sodium methoxide (0.305 mL of a 25 wt. % solution in methanol, 1.335 mmol) and stirred at room temperature for 74.5 hours. The solvent was evaporated under reduced pressure and the residue stirred with ethyl acetate (5 mL) and saturated brine (5 mL) while adjusting the pH of the aqueous layer to 9.4 with 2N hydrochloric acid. The mixture was shaken, the layers separated and the aqueous portion extracted with more ethyl acetate (2×2.5 mL). The combined ethyl acetate solution was washed with brine (5 mL), dried with magnesium sulfate, filtered and evaporated at reduced pressure to afford a white foam (102 mg). This material was shown by $^1$H NMR spectroscopy to consist of a 26:74 mixture of the 9(E) and 9(Z) isomers of 9-deoxo-9-hydroxyiminoerythromycin A.

Method 10: 2.0 LiOH in iPrOH

9-Deoxo-9(E)-hydroxyiminoerythromycin A (279 mg, 0.361 mmol) was added to a partial solution of lithium hydroxide monohydrate (30.3 mg, 0.721 mmol) in isopropanol (2.7 mL), and the mixture was stirred at room temperature in a capped flask. A fine white precipitate formed in a few minutes and, after stiring overnight, the mixture was a hazy suspension. After 21 hours, the mixture was transfered to a freezer at −20° C. and stored there for 15 days. After warming to room temperature, the solvent was evaporated under vacuum and the residue stirred with ethyl acetate (5 mL) and saturated brine (5 mL) while adjusting the pH to 9.2 with dilute hydrochloric acid. The mixture was shaken, the layers separated, and the aqueous phase extracted with more ethyl acetate (2×2.5 ml). The combined ethyl acetate solution was washed with saturated brine (4 mL), dried with magnesium sulfate, filtered and evaporated under vacuum to afford a white foam (249 mg). The product consisted of a 26:74 mixture of 9-deoxo-9(E)-hydroxyiminoerythromycin A and 9-deoxo-9(Z)-hydroxyiminoerythromycin A as determined by $^1$H NMR spectroscopy.

Method 11: 1.0 LiOH in MeCN

A mixture of 9-deoxo-9(E)-hydroxyiminoerythromycin A (500 mg, 0.668 mmol), lithium hydroxide monohydrate (28 mg, 0.668 mmol), and absolute ethanol (5 mL) was stirred at room temperature for 10 minutes to give a solution. The solution was evaporated under reduced pressure to afford a residue that was twice diluted with ethanol (10 mL) and evaporated at reduced pressure and then suspended in anhydrous acetonitrile (5 mL) and evaporated at reduced pressure. The solid residue was suspended in anhydrous acetonitrile (5 mL) and the mixture was stirred at room temperature for 18 days. The solvent was evaporated under reduced pressure and the residue was stirred with ethyl acetate (5 mL) and saturated aqueous sodium chloride solution (5 mL) while adjusting the pH of the aqueous phase to 9.5 by addition of dilute hydrochloric acid. The mixture was shaken, the layers separated, and the aqueous portion was extracted with additional ethyl acetate (2×2.5 mL). The combined ethyl acetate solution was washed with brine (5 mL), dried over magnesium sulfate, filtered and evaporated under reduced pressure to afford a foam (442 mg). This material was shown by $^1$H NMR spectroscopy to consist of a 44:56 mixture of the 9(E) and 9(Z) isomers of 9-deoxo-9-hydroxyiminoerythromycin A.

Method 12: 1.0 LiOH in DMF

A mixture of 9-deoxo-9(E)-hydroxyiminoerythromycin A (500 mg, 0.668 mmol), lithium hydroxide monohydrate (28 mg), and dimethylformamide (5 mL) was stirred at room temperature in a capped flask. After a few hours, the initial suspension gave way to a solution. After stirring for 18 days and 18 hours, the solution was evaporated under reduced pressure and the residue was processed as described in method 11 to afford a foam (402 mg). Analysis of this material by $^1$H NMR spectroscopy indicated a 62:38 mixture of the 9(E) and 9(Z) isomers of 9-deoxo-9-hydroxyiminoerythromycin A.

Method 13: 1.2 LiN(SiMe$_3$)$_2$ in MeCN

A suspension of 9-deoxo-9(E)-hydroxyiminoerythromycin (500 mg, 0.668 mmol) in anhydrous acetonitrile (4 mL) was treated with lithium hexamethyldisilazide (0.80 mL of a 1M solution in hexane, 0.80 mmol). The resulting suspension rapidly gave way to a solution which reformed a suspension after stirring several days at room temperature. After 18 days and 19 hours, the reaction mixture was worked up as described in method 11 to afford a foam (423 mg). This material was shown by $^1$H NMR spectroscopy to be a 50:50 mixture of 9-deoxo-9(E)-hydroxyiminoerythromycin A and 9-deoxo-9(Z)-hydroxyiminoerythromycin A.

EXAMPLE 3

Crystallization of 9-Deoxo-9(Z)-hydroxyiminoerythromycin A

A 3:1 mixture (30.0 g) of 9-deoxo-9(Z)-hydroxyiminoerythromycin A and 9-deoxo-9(E)-hydroxyiminoerythromycin A was added over 2 minutes to well stirred ethyl acetate (60 ml). After obtaining a solution, methylene chloride (120 mL) was rapidly added and the resulting suspension was stirred in an ice bath for one hour. The precipitate was filtered off, washed with methylene chloride (60 mL), and dried under a stream of nitrogen to afford an 86:14 mixture (26.5 g) of of 9-deoxo-9(Z)-hydroxyiminoerythromycin A and 9-deoxo-9(E)-hydroxyiminoerythromycin A.

A solution of the above solid in ethyl acetate (60 mL) was diluted with methylene chloride (120 ml). The resulting suspension was cooled in an ice bath for one hour and then filtered. The collected solid was rinsed with methylene chloride (60 mL) and dried under a stream of nitrogen to afford a 95:5 mixture (23.4 g) of 9-deoxo-9(Z)-hydroxyiminoerythromycin A and 9-deoxo-9(E)-hydroxyiminoerythromycin A.

The Z-isomer of formula (II) is basic and therefore will form acid-addition salts. Pharmaceutically acceptable acid addition salts will be non-toxic salts which can generally be prepared by methods well known to those of ordinary skill in the art.

In general, for preparation of the acid-addition salts, the compound of formula (II) is combined with a stoichiometric amount of an appropriate acid in an inert solvent, and then the salt is recovered by solvent evaporation, or by filtration if the salt precipitates spontaneously, or by precipitation using a cosolvent or a non-polar cosolvent followed by filtration.

Representative salts include the following salts:

| | |
|---|---|
| Acetate | Lactobionate |
| Benzenesulfonate | Laurate |
| Benzoate | Malate |
| Bicarbonate | Maleate |
| Bisulfate | Mandelate |
| Bitartrate | Mesylate |
| Borate | Methylbromide |
| Bromide | Methylnitrate |
| Calcium Edetate | Methylsulfate |
| Camsylate | Mucate |
| Carbonate | Napsylate |
| Chloride | Nitrate |
| Clavulanate | Oleate |
| Citrate | Oxalate |
| Dihydrochloride | Pamoate (Embonate) |
| Edetate | Palmitate |
| Edisylate | Pantothenate |
| Estolate | Phosphate/diphosphate |
| Esylate | Polygalacturonate |
| Ethylsuccinate | Salicylate |
| Fumarate | Stearate |
| Gluceptate | Subacetate |
| Gluconate | Succinate |
| Glucoheptonate | |
| Glutamate | Tannate |
| Glycollylarsanilate | Tartrate |
| Hexylresorcinate | Teoclate |
| Hydrabamine | Tosylate |
| Hydrobromide | Triethiodode |
| Hydrochloride | Valerate |
| Iodide | |
| Isethionate | |
| Lactate | |

The compound of formula II can be used as an intermediate in the synthesis of other macrolide antibiotics. The following examples are given to illustrate synthetic procedures which can be utilized to obtain other macrolides.

EXAMPLE 4

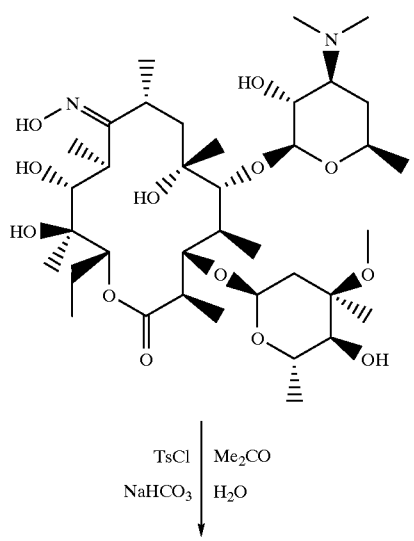

| TsCl | Me$_2$CO |
|---|---|
| NaHCO$_3$ | H$_2$O |

-continued

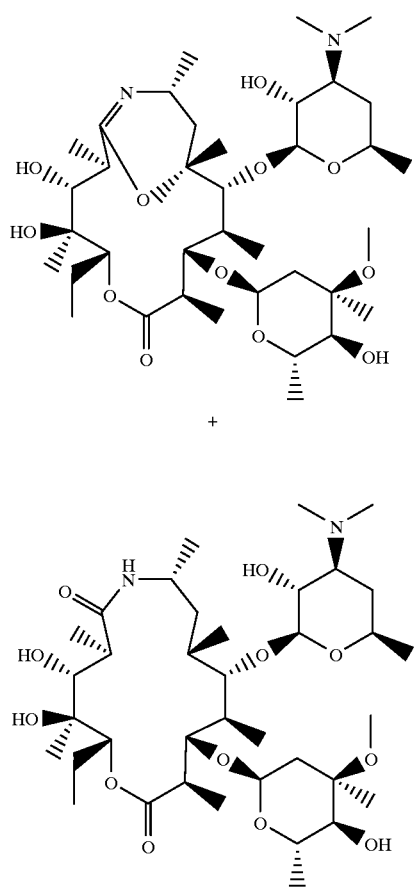

+

Synthesis of 8a-Aza-8a-homoerythromycin A and 9-deoxo-6-deoxy-6,9-epoxy-8a,9-didehydro-8a-aza-8a-homoerythromycin A by the Beckmann Rearrangement of 9-Deoxo-9(Z)-hydroxyiminoerythromycin A 9-Deoxo-9(Z)-hydroxyiminoerythromycin A (200 mg, 0.27 mMol) was dissolved in acetone (2 mL) and the resulting solution was cooled in an ice-bath and stirred under a nitrogen atmosphere. A solution of sodium bicarbonate (84 mg, 1.0 mMol) in water (2 mL) was added followed by the dropwise addition of an acetone solution (2 mL) of p-toluenesulfonyl chloride (100 mg, 0.53 mMol) over 5 minutes.

After stirring for 1.5 hours at 0–5° C., the mixture was diluted with methylene chloride (10 mL) and water (5 mL), and the pH was adjusted from 10 to 5.5 with 2N HCl. The methylene chloride layer was discarded and the aqueous layer was washed with additional methylene chloride (2×10 mL) which was also discarded. Methylene chloride (10 mL) was added to the aqueous layer and the pH was adjusted to 8.5 with 2.5N NaOH. The methylene chloride layer was removed and the aqueous layer was extracted with more methylene chloride (2×20 mL). The combined methylene chloride extracts were dried over anhydrous magnesium sulfate, filtered and evaporated under vacuum to give a mixture of the title compounds as a foam (150 mg).

The above mixture was purified by preparative layer chromatography (two 0.1 mm×20×20 cm Analtech silica gel GF plates, developing and eluting with 60:10:1 methylene chloride-methanol-concentrated ammonium hydroxide) to afford 8a-aza-8a-homoerythromycin A (95 mg, 48% yield) and 9-deoxo-6-deoxy-6-9-epoxy-8a,9-didehydro 8a,9-anhydro-8a-homoerythromycin A (33 mg, 17% yield).

EXAMPLE 5

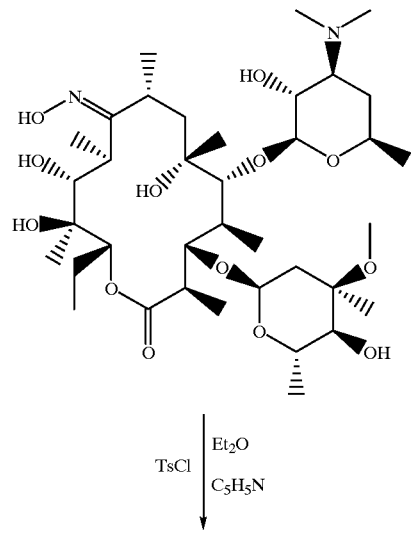

TsCl | Et₂O
C₅H₅N

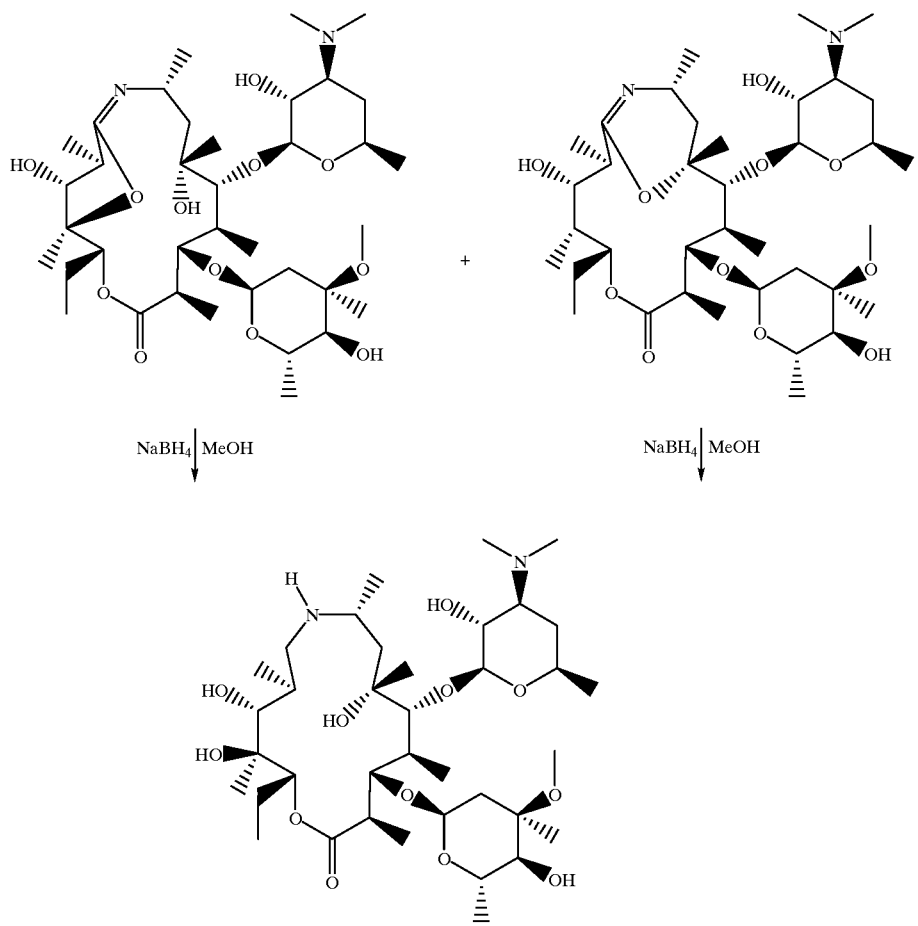

Synthesis of 9-Deoxo-8a-aza-8a-homoerythromycin A via 9-Deoxo-6-deoxy-9,12 -epoxy-8a,9-didehydro 8a-aza-8a-homoerythromycin A and 9-Deoxo-6-deoxy-6,9-epoxy-8a, 9-didehydro-8a-aza-8a-homoerythromycin A 9-Deoxo-9(Z)-hydroxyiminoerythromycin A (5 g, 6.68 mMol) was dissolved in ice-cold pyridine (50 mL) and to this solution was added an ethyl ether (25 mL) solution of p-toluenesulfonyl chloride (2.5 g, 13.1 mmol) over 10 minutes. The solution was stirred with ice-bath cooling for 2 hours, whereupon the solvents were evaporated under vacuum. The residue was partitioned between water (200 mL) and methylene chloride (200 mL). The methylene chloride was discarded and more methylene chloride (200 mL) was added. The pH of the mixture was adjusted to 5.5 with 2.5N sodium hydroxide and the methylene chloride wash was removed. More methylene chloride (200 mL) was added and the pH of the mixture was adjusted from 5.3 to 6.0 with 2.5N sodium hydroxide. The methylene chloride wash was removed and more methylene chloride (200 mL) was added. The pH of the mixture was adjusted from 5.8 to 9.5 with 2.5N sodium hydroxide. The methylene chloride extract was removed and the aqueous layer was re-extracted with more methylene chloride (2×200 mL). The combined extracts from the pH 9.5 mixture were dried over anhydrous magnesium sulfate, filtered and evaporated under vacuum to provide a 3:1 mixture of 9-deoxo-6-deoxy-9,12-epoxy-8a, 9-didehydro-8a-aza-8a-homoerythromycin A and 9-deoxo-6-deoxy-6,9-epoxy-8a,9-didehydro-8a-aza-8a-homoerythromycin A as a light yellow foam (4 g).

A solution of the foam in methanol (100 mL) was cooled in an ice-bath and treated with sodium borohydride (2.5 g, 66 mMol) in portions over 1 hour. The resulting solution was stirred an additional 2 hours with ice-bath cooling and then overnight at room temperature.

The pH of the methanol solution was adjusted from 10.5 to 2.5 with 2N hydrochloric acid. After 5 minutes, the pH of the solution was brought to 6 with 5N sodium hydroxide and the solvents were removed under vacuum. The residue was stirred with water (200 mL) and methylene chloride (200 mL) while the pH of the aqueous phase was adjusted to 6.5 with 5N sodium hydroxide. The methylene adjusted to 7.0 with 5N sodium hydroxide. The methylene chloride was removed and more methylene chloride (200 mL) was added. The pH of the mixture was chloride phase was discarded, fresh methylene chloride (200 mL) was added to the aqueous phase, and the mixture was stirred while the pH was adjusted to 9.5 with 5N sodium hydroxide. The methylene chloride extract was removed and the aqueous layer was re-extracted with more methylene chloride (2×200 mL). The combined extracts from the pH 9.5 mixture were dried with anhydrous magnesium sulfate, filtered and evaporated under vacuum to give the crude product as a foam (3.4 g).

The title compound was crystallized by dissolving the above foam in ethanol (12 mL), diluting the solution with deionized water (12 mL) and stirring overnight. The resulting suspension was filtered and the collected solids rinsed with a 2:1 water-ethanol mixture (2 mL) and dried under a stream of nitrogen to afford 9-deoxo-8a-aza-8a-homoerythromycin A (1.15 g) as a white solid.

EXAMPLE 6

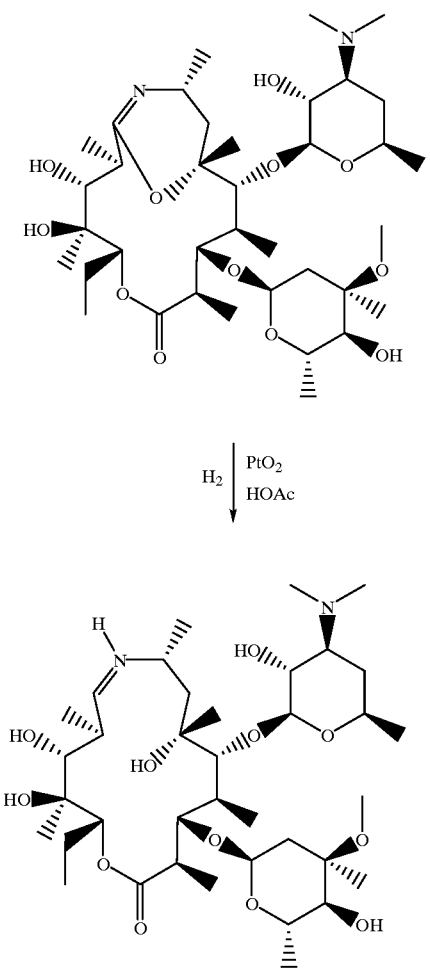

Synthesis of 9-Deoxo-8a-aza-8a-homoerthromycin A

A mixture of 9-deoxo-6-deoxy-6,9-epoxy-8a,9-didehydro 8a-aza-8a-homoerythromycin A (100 mg), acetic acid (4 mL) and platinum oxide (120 mg) was hydrogenated overnight at 2000 psi. The mixture was filtered through celite and the filtrate evaporated under vacuum to a residue which was partitioned between methylene chloride (12 mL) and saturated sodium bicarbonate (5 mL). The methylene chloride was removed and the aqueous layer re-extracted with methylene chloride (2×5 mL). The combined methylene chloride extracts were dried over anhydrous magnesium sulfate, filtered and evaporated under vacuum to an oil (60 mg).

The oil was purified by preparative thin-layer chromatography (Analtech 0.1 mm×20×20 cm basic alumina plate, developing and eluting with 5% methanol in methylene chloride) to give the title compound as a white foam (42 mg, 42% yield).

EXAMPLE 7

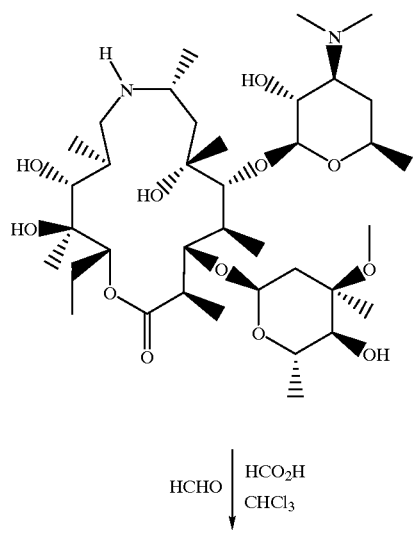

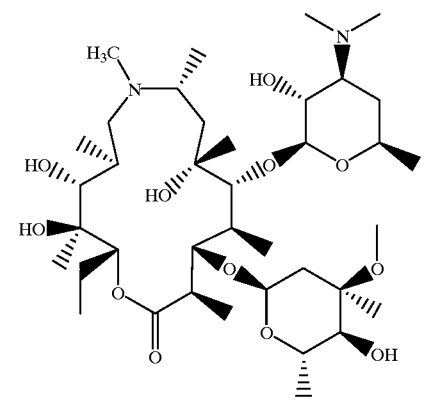

Synthesis of 9-Deoxo-8a-aza-8a-methyl-8a-homoerythromycin A

A solution of 9-deoxo-8a-aza-8a-homoerythromycin A (1.00 g, 1.36 mMol) in chloroform (6 mL) was treated with 37% aqueous formaldehyde (0.102 mL, 1.36 mMol) and 98% formic acid (0.106 mL, 2.76 mMol). The resulting solution was heated at reflux for 48 hours, then cooled to room temperature and added to a well-stirred mixture of water (50 mL) and methylene chloride (50 mL). After adjusting the pH of the aqueous phase from 5.4 to 5.1 with 1N hydrochloric acid, the methylene chloride layer was removed and more methylene chloride (50 mL) was added. The pH was adjusted to 6.0 with 1N sodium hydroxide, the methylene chloride was removed, and more methylene chloride (50 mL) was added. The pH was then brought to 8.6 with 1N sodium hydroxide, the methylene chloride extract was removed and the aqueous layer was re-extracted with more methylene chloride (2×50 mL). The combined methylene chloride extracts from the pH 8.6 aqueous mixture were dried over anhydrous magnesium sulfate, filtered and evaporated under vacuum to a foam (735 mg).

A solution of the foam in ethanol (5 mL) was concentrated to ca. 3 mL volume and diluted with deionized water (2 mL). After stirring 2 hours, the resulting suspension was filtered and the collected solid was rinsed with cold 1:1 ethanol-water (6 mL) and dried under a stream of nitrogen to give the title compound (590 mg, 58% yield) as a white solid.

As an antibiotic, the compound of formula (II) can be administered in such oral dosage forms as tablets, capsules, pills, powders, granules, elixirs, tinctures, suspensions, syrups and emulsions. Like-wise, it may also be administered in intravenous, intraperitoneal, subcutaneous or intramuscular form, all using forms well known to those of ordinary skill in the pharmaceutical arts. In general, the preferred form of administration is oral. An effective but non-toxic amount of the compound can be employed as a mammalian antibiotic.

The dosage regimen utilizing the compound of formula (II) is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Dosages of the compound of formula (II), when used for the indicated effects, will range between about 0.2 mg per kg of body weight per day (mg/kg/day) to about 120 mg/kg/day and preferably 10–50 mg/kg/day. Advantageously, the compound may be administered in a single daily dose, or the total daily dosage may be administered in divided doses of two, three or four times daily.

Furthermore, the compound of formula (II) can be administered in topical, otic or ophthalmic form via use of suitable vehicles.

In the methods of using compound (II), that compound can form the active ingredient, and is typically administered in admixture with suitable pharmaceutical diluents, excipients or carriers (collectively referred to herein as "carrier" materials) suitably selected with respect to the intended form of administration, that is, oral tablets, capsules, elixirs, syrups, and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol, and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Disintegrators include, without limitation, starch, methyl cellulose, agar, bentonite, xanthan gum, and the like.

The compound of formula (II) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compound of formula (II) may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the compound of formula (II) may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The test procedures employed to measure this activity of the compound of formula (II) are described below.

EXAMPLE 8

The antibacterial activity of 9-deoxo-9(Z)-hydroxyiminoerythromycin A (II) against a panel of aerobic Gram positive and negative bacteria is shown in the following Table. The assay employs a liquid turbidimetric microtiter method for determination of the minimum inhibitory concentration (MIC) in brain heart infusion broth. The MIC endpoint in mcg/ml is defined as the lowest concentration of test compound that completely inhibits the growth (absence of detectable turbidity) of bacteria. The MIC is generally not an absolute value but rather a concentration range that falls within a two-fold dilution limit. Generally twelve two-fold dilutions of the test compound are employed with the initial concentration set at 128 mcg/ml. As can be seen from the Table, the activity of the 9(Z)-oxime is comparable with the activities of the known compounds 9-deoxo-9(E)-hydroxyiminoerythromycin A (III) and erythromycin A (I).

TABLE I

In vitro Activity of Compound (1) and Related Compounds

| | | MIC Values (mcg/ml) | | |
|---|---|---|---|---|
| Microorganism | | (II) | (III) | (I) |
| Enterococcus faecalis | MB 5407 | 2 | 0.5 | 1 |
| Enterococcus faecium | MB 5416 | 0.25 | 0.12 | 0.12 |
| Streptococcus agalactiae | CL 1343 | ≦0.06 | ≦0.06 | ≦0.06 |
| Staphylococcus aureus | MB 2865 | 0.25 | 0.25 | 0.25 |
| Staphylococcus epidermidis | MB 5414 | 0.12 | 0.12 | 0.12 |
| Staphylococcus haemolyticus | MB 5412 | 0.12 | 0.12 | 0.12 |
| Steptococcus pneumoniae | CL 2883 | ≦0.06 | 0.12 | ≦0.06 |
| Streptococcus pyogenes | MB 2874 | ≦0.06 | ≦0.06 | ≦0.06 |
| Streptococcus pyogenes | MB 5406 | 32 | 16 | 16 |
| Streptococcus viridans | CL 2943 | ≦0.06 | ≦0.06 | ≦0.06 |
| Escherichia coli | MB 2884 | 16 | 32 | 16 |
| Escherichia coli | MB 4926 | 0.5 | 0.25 | 0.25 |
| Klebsiella pneumoniae | MB4005 | 32 | 32 | 32 |
| Yersinia enterocoltica | CL 1598 | 32 | 16 | 32 |
| Pseudomonas stutzeri | MB 1231 | ≦0.06 | 1 | ≦0.06 |

(II) 9-Deoxo-9(Z)-hydroxyiminoerythromycin A
(III) 9-Deoxo-9(E)-hydroxyiminoerythromycin A
(I) Erythromycin A
† An undetermined fraction of the (Z)-isomer is converting to the (E)-isomer under the assay conditions.

The compound of formula (II) is useful as an antibacterial agent both in vitro and in vivo, and its spectrum of activity is similar to that of erythromycin A. Consequently, it can be used for the same purposes, and, in the same manner, as erythromycin A. In general, the antibacterial compound of formula II and salts thereof, exhibits in vitro activity against a variety of Gram-positive microorganisms, e.g. Staphylococcus aureas and Streptococcus pyogenes, and against certain Gram-negative microorganisms such as those of spherical or ellipsoidal shape (cocci). Their activity is readily demonstrated by in vitro tests against various microorganisms. Their in vitro activity renders them useful for topical application; for sterilization purposes, e.g., sickroom utensils; and as industrial antimicrobials, for example, in water treatment, slime control, and preservation of paint and wood. The extrapolation of such in vitro tests to support for such utilities for macrolide compounds is taught in U.S. Pat. No. 4,518,590. For in vitro use for topical application, it will usually be convenient to prepare pharmaceutical compositions, in which the compound for formula III is combined with a pharmaceutically-acceptable carrier or diluent, for example, in the form of ointments and creams. Appropriate carriers and diluents for these purposes include mineral oils and vegetable oils, and solvents such as water, alcohols, and glycols, and mixtures thereof. Such a pharmaceutical composition will normally contain the pharmaceutically-acceptable carrier and the compound of formula II in a weight ratio in the range from 4:1 to 1:200.

Additionally, the antibacterial compound of formula II, and the pharmaceutically-acceptable salts thereof are active in vivo versus a variety of Gram-positive microorganisms, e.g. *Staphylococcus aureaus* and *Streptococcus pyogenes*, and also certain Gram-negative microorganisms, via the oral and parenteral routes of administration in animals, including man. Its in vivo activity is more limited than its in vitro activity as regards susceptible organisms, and it is determined by the usual procedure which comprises infecting mice of substantially uniform weight with the test organism and subsequently treating them orally or subcutaneously with the test compound. Extrapolation of such in vivo tests to support for human utility for macrolide compounds is likewise taught in U.S. Pat. No. 4,518,590, cited above.

While the invention has been described and illustrated in reference to certain preferred embodiments thereof, those skilled in the art will appreciate that various changes, modifications and substitutions can be made therein without departing from the spirit and scope of the invention.

It is intended, therefore, that the invention be limited only by the scope of the claims which follow and that such claims be interpreted as broadly as is reasonable.

What is claimed is:

1. A method of making an erythromycin Z oxime compound of the formula:

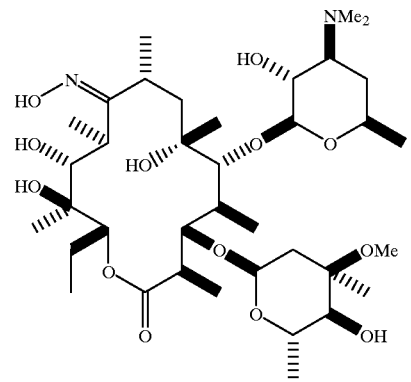

comprising reacting an erythromycin E oxime starting compound of the formula:

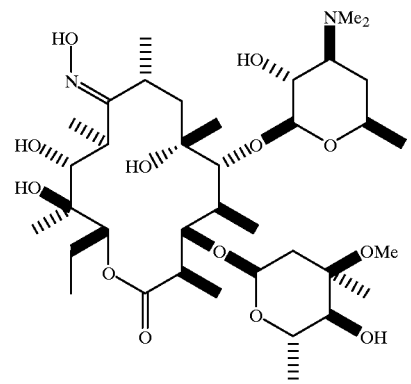

with a base selected from the group consisting of lithium hydroxide, sodium hydroxide, lithium methoxide, sodium ethoxide, sodium ethoxide and lithium hexamethyldisilazide in the presence of a solvent selected from the group consisting of methanol, ethanol, isopropanol, acetonitrile and dimethylformamide, wherein said base is present at a concentration of from 1 to 10 molar equivalents, said reaction taking place within a temperature range of 0° C. to 80° C.

* * * * *